(12) United States Patent
Glaser

(10) Patent No.: US 11,065,373 B2
(45) Date of Patent: Jul. 20, 2021

(54) WATER PREPARATION SYSTEM FOR DIALYSIS TREATMENTS

(71) Applicant: FRESENIUS MEDICAL CARE DEUTSCHLAND GMBH, Bad Homburg (DE)

(72) Inventor: Benedict Glaser, Schweinfurt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 5 days.

(21) Appl. No.: 15/754,147

(22) PCT Filed: Sep. 9, 2016

(86) PCT No.: PCT/EP2016/071276
§ 371 (c)(1),
(2) Date: Feb. 21, 2018

(87) PCT Pub. No.: WO2017/042319
PCT Pub. Date: Mar. 16, 2017

(65) Prior Publication Data
US 2018/0236156 A1    Aug. 23, 2018

(30) Foreign Application Priority Data

Sep. 10, 2015   (DE) .................... 10 2015 217 281.3

(51) Int. Cl.
*A61M 1/16*   (2006.01)
*C02F 1/44*   (2006.01)
(Continued)

(52) U.S. Cl.
CPC ........ *A61M 1/1662* (2014.02); *A61M 1/1656* (2013.01); *A61M 1/1672* (2014.02);
(Continued)

(58) Field of Classification Search
CPC .... A61M 1/1647; A61M 1/165; A61M 1/166; A61M 1/1664; A61M 1/168;
(Continued)

(56) References Cited

U.S. PATENT DOCUMENTS 4,284,492 A * 8/1981 Karn .................... B01D 61/022
                                                204/631
5,312,547 A * 5/1994 Kruger .................... A61M 1/28
                                                210/317
(Continued)

FOREIGN PATENT DOCUMENTS

DE        3941131 C1    5/1991
DE        19926901 A1   1/2001
(Continued)

OTHER PUBLICATIONS

International Preliminary Report on Patentability issued in corresponding International Patent Application No. PCT/EP2016/071276 dated Mar. 22, 2018 (11 pages).
(Continued)

*Primary Examiner* — Nam X Nguyen
*Assistant Examiner* — Ekandra S. Miller-Cruz
(74) *Attorney, Agent, or Firm* — Kilyk & Bowersox, P.L.L.C.

(57) ABSTRACT

The invention relates to a water treatment system (1) for dialysis treatments, wherein the water treatment system (1) comprises a permeate circuit with a reverse osmosis system (RO) and at least one tap ($ES_{1, 2 \ldots N}$) for permeate, whereby the reverse osmosis system (RO) is fed by the reflux of the at least one tap ($ES_{1, 2 \ldots N}$) for dialysis treatments and/or a raw water inflow (RZ), whereby the water treatment system further comprises a heat exchanger (WT), whereby a primary circuit (PK) of the heat exchanger (WT) is connected with a buffer tank (PT) for storing thermal energy,
(Continued)

whereby a second circuit (SK) of the heat exchanger (WT) is integrated into the permeate circuit, whereby heat is transferred in a controlled manner from the buffer tank (PT) via the heat exchanger (WT) to permeate in the permeate circuit.

11 Claims, 1 Drawing Sheet

(51) Int. Cl.
    *C02F 1/00*     (2006.01)
    *C02F 1/14*     (2006.01)
    *B01D 61/02*     (2006.01)
    *C02F 103/02*     (2006.01)
    *C02F 103/04*     (2006.01)

(52) U.S. Cl.
    CPC ......... *A61M 1/1686* (2013.01); *B01D 61/025* (2013.01); *C02F 1/008* (2013.01); *C02F 1/14* (2013.01); *C02F 1/441* (2013.01); *A61M 2205/366* (2013.01); *C02F 2103/026* (2013.01); *C02F 2103/04* (2013.01); *C02F 2209/001* (2013.01); *C02F 2209/003* (2013.01); *C02F 2209/02* (2013.01); *C02F 2209/40* (2013.01); *Y02A 20/212* (2018.01)

(58) Field of Classification Search
    CPC .............. A61M 1/1682; A61M 1/1688; A61M 1/1694; A61M 1/308; A61M 1/1662; A61M 1/1672; A61M 1/1686; A61M 1/1656; A61M 2205/366; A61M 2205/3331; A61M 2205/3368; B01D 61/022; B01D 61/10; B01D 61/12; B01D 61/30; B01D 2313/083; B01D 2313/90; B01D 61/025; B01D 61/32; C02F 1/44; C02F 2203/002; C02F 1/14; C02F 1/008; C02F 1/441; C02F 2209/40; C02F 2209/02; C02F 2209/001; C02F 2103/04; C02F 2209/003; C02F 2103/026; Y02A 20/212
    USPC .... 210/87, 175, 321.71, 652, 900, 645–647; 604/4.01, 5.01, 6.01, 6.09
See application file for complete search history.

(56) References Cited

U.S. PATENT DOCUMENTS

| | | | | |
|---|---|---|---|---|
| 6,325,935 | B1* | 12/2001 | Hojsgaard | C02F 11/04 165/299 |
| 2003/0094406 | A1* | 5/2003 | Smith | B01D 61/022 210/96.2 |
| 2007/0102357 | A1* | 5/2007 | Weatherill | A61L 2/04 210/636 |
| 2009/0134080 | A1* | 5/2009 | Fabig | B01D 61/022 210/137 |
| 2010/0192686 | A1* | 8/2010 | Kamen | A61M 1/365 73/290 R |
| 2011/0300231 | A1* | 12/2011 | Peterson | B01D 61/58 424/600 |
| 2012/0298569 | A1* | 11/2012 | Volker | B01D 65/02 210/198.1 |
| 2014/0151297 | A1* | 6/2014 | Hulme | B01D 65/02 210/636 |
| 2015/0021245 | A1* | 1/2015 | Rohde | A61M 1/1629 210/87 |
| 2015/0021248 | A1* | 1/2015 | Alvensleben | A61M 1/1664 210/149 |
| 2015/0231571 | A1* | 8/2015 | Volker | A61M 1/166 210/636 |

FOREIGN PATENT DOCUMENTS

| | | | | |
|---|---|---|---|---|
| DE | 19933223 | A1 * | 1/2001 | ............... A61L 2/04 |
| DE | 202010006823 | U1 | 9/2011 | |
| EP | 1236685 | A2 * | 9/2002 | ......... A61M 1/1686 |
| EP | 1236685 | A2 | 9/2002 | |
| KR | 100435831 | B1 * | 6/2004 | ................ F24J 2/04 |
| WO | WO-2001089996 | A2 * | 5/2001 | ............. B01D 61/08 |
| WO | 0141895 | A1 | 6/2001 | |
| WO | WO0141895 | A1 * | 6/2001 | ............. A61L 2/04 |
| WO | 0189996 | A2 | 11/2001 | |
| WO | 2007045015 | A1 | 4/2007 | |
| WO | WO2012175210 | A2 * | 12/2012 | ............. A61M 1/14 |

OTHER PUBLICATIONS

International Search Report and Written Opinion issued in corresponding International Patent Application No. PCT/EP2016/071276 (with English translation of International Search Report) dated Dec. 6, 2016 (17 pages).
Examination Report issued in corresponding German Patent Application No. 10 2015 217 281.3 dated Mar. 21, 2016 (10 pages).

* cited by examiner

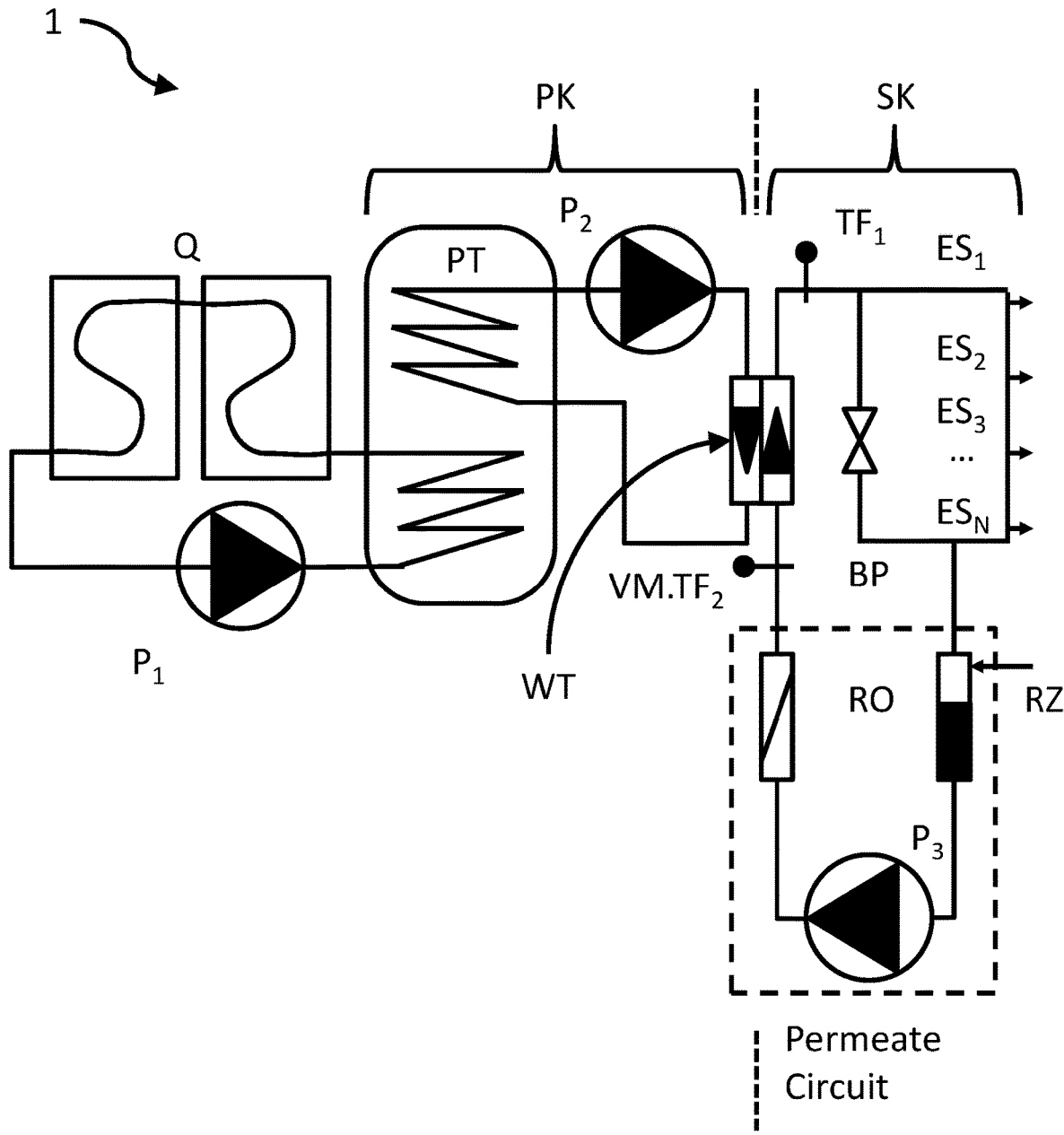

WATER PREPARATION SYSTEM FOR DIALYSIS TREATMENTS

This application is a National Stage Application of PCT/EP2016/071276, filed Sep. 9, 2016, which claims priority to German Patent Application No. 10 2015 217 281.3, filed Sep. 10, 2015.

BACKGROUND OF THE INVENTION

Ultrapure water—also referred to as permeate—is required in many fields of applied medicine.

Ultrapure water is for instance required for the treatment of dialysis patients. Generally, permeate is prepared from raw water through a special form of filtration, an ultra-filtration according to the principle of reverse osmosis. Subsequently, the water is provided through a circulation line to the respective taps. Appropriate taps may be the applicant's dialysis machines 5008, 4003 or GENIUS Preperator etc.

It may also occur that a considerable amount of permeate is required in a relatively short period of time. In these cases, e.g a buffer can be included that is provided by the applicant e.g. under the designation Aquator 500 L or 1000 L. However, then warming the permeate to a near-body temperature (e.g. 34 degrees Celsius) is intended in order to be able to reduce the heating energy at the taps.

Since even ultrapure water may suffer from loss of quality when remaining in a conduit for a longer period of time, the ultrapure water in a circulation line is constantly kept in motion.

However, a fundamental problem is maintaining the hygiene.

The prior art has included disinfection of the systems by chemical means either regularly or when limiting values for biological pollution are exceeded.

Yet, this proves to be time-consuming since subsequently the disinfecting solution also needs to be removed residue-free. Moreover, this procedure can only be completely automated in exceptional cases. During this time it is normally impossible to tap ultrapure water. This causes a huge problem especially for the treatment centres and their patients.

Therefore several attempts have been made in the past to replace chemical disinfection with thermal disinfection. These disinfection methods are also known as heat disinfection.

For example, heat disinfection of a water supply system is known from DE 600 20 268 T2, and a method for heat disinfection of haemodialysis systems is known from DE 199 33 223 B4.

Thereby, the problem often arises that the system must be quickly heated, so that an appropriate electrical power input must be provided.

In order to address this problem, in the past often only the circulation line has been heat disinfected, i.e. the storage tanks and/or taps have not been disinfected.

Until now, heat exchangers in combination with a low-pressure boiler have often been utilised in these systems with the permeate being heated in the heat exchanger.

Other approaches have been to keep the permeate in a tank at a near-body temperature with less electric power being required and where it is warmed over a longer period of time in order to avoid a short-term high power draw. In this regard, it should be noted that electric power supply is not constantly available in all parts of the world and that electric installations are often only provided insufficiently so that a short-term high power draw is normally to be avoided so as not to risk a shut-down of other devices in a clinical environment or even risk fires because of overloaded lines.

However, the tank in particular causes a problem for heat disinfection, since it comprises a high volume and a large surface and is difficult to be heat disinfected.

Although it would be possible to empty the tank at least partially for the heat disinfection, it would then no longer serve to accomplish the complete disinfection of the hot water storage.

Alternatively, the tank can—as already mentioned—be completely excluded from the disinfection with the help of a bypass line. However, this is questionable also from a hygienic point of view.

BRIEF SUMMARY OF THE INVENTION

In the light of the background of the invention cited above, it is an object of the invention to provide an improved water treatment system that enables hygienic provisioning of permeate.

The problem is solved by a water treatment system for dialysis treatments with the water treatment system comprising a permeate circuit with a reverse osmosis system and at least one tap for permeate. In the process, the reverse osmosis system is fed by the reflux of the at least one tap for dialysis treatments and/or a raw water inflow. The water treatment system further comprises a heat exchanger wherein a primary circuit of the heat exchanger is connected with a buffer tank to store thermal energy, and wherein a secondary circuit of the heat exchanger is integrated into the permeate circuit, wherein heat is transferred in a controlled manner from the buffer tank via the heat exchanger to permeate in the permeate circuit.

Further advantageous embodiments of the invention are subject of the dependent claims and their description.

BRIEF DESCRIPTION OF THE DRAWINGS

In FIG. 1 a schematic diagram according to the embodiments of the invention is illustrated.

DETAILED DESCRIPTION OF THE INVENTION

Subsequently, the invention will be presented in greater detail with reference to the FIGURE. It is to be noted that different aspects will be depicted that can be employed individually or in combination with each other. i.e. any aspect can be utilised with different embodiments of the invention if not explicitly presented simply as an alternative.

Moreover, to simplify matters hereinafter normally only one entity will be referred to. Unless explicitly stated otherwise, the invention may also comprise several of the concerned entities respectively. In this respect, the usage of the terms "a" or "an" is only indicative as to that in a simple embodiment at least one entity is used.

In a water treatment system 1 according to the present invention for dialysis treatments the water treatment system 1 comprises a permeate circuit with a reverse osmosis system (RO) and at least one tap $ES_1$ or more than one taps $ES_2 \ldots {}_N$ for permeate.

The reverse osmosis system RO may be fed on the one hand by the reflux from the at least one tap $ES_1$ or more than one taps $ES_2 \ldots N$ for dialysis treatments, or on the other hand alternatively or additionally by a raw water inflow RZ.

The water treatment system further comprises a heat exchanger WT. A primary circuit PK (primary circuit) of the heat exchanger WT is connected with a buffer tank PT wherein the buffer tank is installed to store thermal energy. A secondary circuit SK (secondary circuit) of the heat exchanger WT is, however, integrated into the permeate circuit, wherein heat is now transferred in a controlled manner from the buffer tank PT via the heat exchanger WT to permeate in the permeate circuit.

I.e. the invention allows to keep the volume that is to be disinfected small, whereas at the same time the option is provided to bring on the one hand large volumes of provided permeate to near-body temperatures with the help of the heat exchanger WT or on the other hand to also rapidly provide high temperatures for heat disinfection, whereby all system parts through which permeate flows can now be heat disinfected.

In one embodiment of the invention the temperature of the permeate is increased to a temperature from 20 degrees Celsius up to 37 degrees Celsius after the passage of the heat exchanger WT in a first operational mode of the water treatment system (1) for dialysis treatments. Hereby the heating power of devices at the taps $ES_{1, 2 \ldots N}$ can be lowered which makes these devices more cost-effective in operation and production.

In another embodiment of the invention, the temperature of the permeate is increased to a temperature of 70 degrees Celsius and more after the passage of the heat exchanger (WT) in a second operational mode of the water treatment system (1) for hygienic treatment of at least parts of the permeate circuit. In particular, the temperature can be increased to 85 degrees Celsius or up to over 100 degrees Celsius in order to thus provide a quicker heat disinfection. Thereby e.g. the execution time of the second operation mode can be dependent on the temperature the permeate comprises ahead of and/or behind the heat exchanger.

Of particular advantage is that in one embodiment the invention can also comprise a solar thermal or geothermal source or a phase change storage to feed the buffer tank (PT) with thermal energy. In FIG. 1, for instance, feeding via solar collectors is suggested. Hereby areas in which continuous supply of electrical energy is a problem or that dispose of a suitable energy supply can be suitably provided with thermal energy for the buffer tank PT. In particular, the degrees of efficiency of directly consumed thermal energy are considerably higher than a conversion from electrical energy. A pump $P_1$ can also be provided for circulation.

Without loss of generality of the invention, the permeate circuit may further comprise a bypass BP to shorten the permeate circuit, wherein the bypass is arranged for bypassing the at least one tap ($ES_{1, 2 \ldots N}$) for dialysis treatments. This can be an advantage for certain operating modes of the water treatment system 1.

In another embodiment of the invention the heat exchanger WT comprises a degree of efficiency of 75% and more. In particular, the heat exchanger WT comprises a degree of efficiency of 90% and more.

Without loss of generality, the permeate circuit may comprise a buffer storage for permeate or may not comprise any buffer storage for permeate. In this respect, there are no limits for the system design. It is advantageous that for instance the buffer tank PT only needs to be adjusted to the heating power that is to be provided, whereas a possibly existing buffer tank for permeate only needs to be adjusted to the amount of permeate that is to be provided and the cleaning capacity of the reverse osmosis RO. I.e. the invention permits a highly flexible system design so that the invention can be utilised in a variety of application scenarios.

In another embodiment of the invention, a first temperature sensor $TF_1$ is arranged after the outlet of the secondary circuit SK. Then the inflow of the primary circuit PK to the heat exchanger WT can be controlled in dependence on the permeate circuit outlet temperature $T_{PKout}$ measured by the first temperature sensor $TF_1$ so that a required target temperature, for instance near-body temperature or temperature for heat disinfection will be reached.

For instance, the pump $P_2$ can be controlled respectively.

Alternatively or additionally a second temperature sensor ($TF_2$) can be arranged in front of the inlet of the secondary circuit (SK), wherein the inflow of the primary circuit (PK) to the heat exchanger (WT) is controlled also in dependence on the permeate circuit inlet temperature ($T_{PKin}$) measured by the second temperature sensor ($TF_2$). In particular, if a first temperature sensor $TF_1$ as well as a second temperature sensor $TF_2$ are provided, entering the temperature into the heat exchanger via the first circuit can be controlled in a particularly precise manner.

Furthermore it can be provided that in embodiments of the invention a flow meter VM is arranged in the secondary circuit SK. The exact place of the flow meter can thereby be suitably selected and does not have to be selected as shown in FIG. 1. In particular, a flow meter VM can also be arranged at the place of a possibly existing temperature sensor $TF_1$, $TF_2$. Now, alternatively or additionally also in dependence on the volume measured by the flow meter (VM) the inflow of the primary circuit PK to the heat exchanger WT can be controlled.

For instance, the flow meter can also be provided by a pump $P_3$.

I.e. the embodiments of the invention allow a hygienic design of a water treatment system, since the separation of the permeate circuit and the buffer tank permits a more compact design of the permeate circuit in combination with simpler disinfectability of the permeate circuit.

Although only one heat exchanger WT has been displayed above, for efficiency reasons of course also two or more heat exchangers can be provided for the permeate circuit. Thus for instance a first heat exchanger can be optimised for heat supply for a first operational mode, whereas a second heat exchanger is optimised for heat supply for a second operational mode. I. e. the heat exchangers are for instance optimised with regard to the operating parameters and the respective degree of efficiency. Obviously it may also be provided for this type of system configuration that each heat exchanger is fed by its own primary circuit with its own buffer tank. However, it may also be provided that both heat exchangers are fed from a shared primary circuit with only one buffer tank.

I.e. the invention is characterised by a hydraulic separation. The volume and the inner surface of the permeate circuit are thus noticeably decreased which significantly improves the disinfectability and significantly reduces the energy necessary to reach the temperature that is required for the heat disinfection.

The buffer tank PT serves in the system of the invention exclusively as energy storage, i.e. tapping permeate from the tank is not possible.

Since the buffer tank buffers the energy required for a heat disinfection, it can be slowly warmed whereby the required power can be reduced. As the volume in the permeate circuit may be kept low, the permeate can quickly be heated up to the heat disinfection temperature. Furthermore, by means of a higher temperature that is possible because of the lower volume also the duration for a complete circulation line disinfection is reduced.

The invention claimed is:

1. A water treatment system for dialysis treatments, which comprises:
    a first heat exchange circuit, a second heat exchange circuit, a heat exchanger, and a buffer tank,
    the buffer tank being in thermal communication with both the first heat exchange circuit and the second heat exchange circuit and being configured exclusively for storing thermal energy,
    the second heat exchange circuit being separate from the first heat exchange circuit and configured to feed the buffer tank with thermal energy from, and exchange heat with, a thermal energy source, and the heat exchanger being separate from the buffer tank;
    at least one tap;
    a reverse osmosis system; and
    a permeate circuit hydraulically separated from the buffer tank such that it is not possible to tap permeate from the buffer tank,
    wherein the first heat exchange circuit is configured to transfer thermal energy from the buffer tank to the heat exchanger, the heat exchanger is configured to transfer heat in a controlled manner from the first heat exchange circuit to permeate in the permeate circuit, the permeate circuit is configured to introduce raw water, reflux from the at least one tap, or both, into the reverse osmosis system to produce permeate from said raw water, from said reflux, or from both, prior to passing said permeate into the heat exchanger, and the heat exchanger is integrated into the permeate circuit,
    wherein the heat exchanger comprises a primary circuit inlet, a primary circuit outlet, a secondary circuit inlet, and a secondary circuit outlet, and
    wherein the heat exchanger is disposed in between the reverse osmosis system and the at least one tap such that the water treatment system is configured to flow permeate from the reverse osmosis system to the secondary circuit inlet of the heat exchanger, through the heat exchanger, and out of the secondary circuit outlet of the heat exchanger to deliver permeate heated by the heat exchanger to the at least one tap.

2. The water treatment system for dialysis treatments according to claim 1, wherein, in a first operational mode of the water treatment system for dialysis treatments, the water treatment system is configured to increase a temperature of the permeate from 20 degrees Celsius up to 37 degrees Celsius after the passage of the permeate through the heat exchanger.

3. The water treatment system for dialysis treatments according to claim 2, wherein, in a second operational mode of the water treatment system, the water treatment system is configured to increase a temperature of the permeate to a temperature of from 70 degrees Celsius to 100 degrees Celsius after the passage of the permeate through the first heat exchanger, thereby hygienically treating at least parts of the permeate circuit.

4. The water treatment system for dialysis treatments according to claim 1, wherein the second heat exchange circuit comprises a solar thermal or geothermal source or a phase change storage to feed the buffer tank with thermal energy.

5. The water treatment system for dialysis treatments according to claim 1, wherein the first heat exchanger comprises a degree of efficiency of 75% or more.

6. The water treatment system for dialysis treatments according to claim 1, wherein the permeate circuit does not have a thermal buffer storage for permeate.

7. The water treatment system for dialysis treatments according to claim 1, further comprising a first temperature sensor in the permeate circuit located after the secondary circuit outlet of the heat exchanger, wherein an inflow of the first heat exchange circuit to the heat exchanger is controlled in dependence on a permeate circuit outlet temperature measured by the first temperature sensor.

8. The water treatment system for dialysis treatments according to claim 1, further comprising a second temperature sensor in the permeate circuit located ahead of the secondary circuit inlet of the heat exchanger, wherein an inflow of the first heat exchange circuit to the first heat exchanger is controlled in dependence on a permeate circuit inlet temperature measured by the second temperature sensor.

9. The water treatment system for dialysis treatments according to claim 1, further comprising a flow meter in the permeate circuit, wherein an inflow of the first heat exchange circuit to the first heat exchanger is controlled in dependence on a volume measured by the flow meter.

10. The water treatment system for dialysis treatments according to claim 1, wherein the water treatment system is configured for hydraulic separation, a volume and an inner surface of the permeate circuit are configured to disinfect a low volume of permeate or to heat a large volume of permeate to a temperature of from 20 degrees Celsius up to 37 degrees Celsius or from a temperature of from 70 degrees Celsius to 100 degrees Celsius.

11. The water treatment system for dialysis treatments according to claim 1, wherein the permeate circuit further comprises a bypass in between the heat exchanger and the at least one tap, the bypass shortens the permeate circuit, and the bypass joins with reflux from the at least one tap to direct permeate back to the reverse osmosis system.

* * * * *

UNITED STATES PATENT AND TRADEMARK OFFICE
CERTIFICATE OF CORRECTION

PATENT NO.         : 11,065,373 B2
APPLICATION NO.    : 15/754147
DATED              : July 20, 2021
INVENTOR(S)        : Glaser Page 1 of 1

It is certified that error appears in the above-identified patent and that said Letters Patent is hereby corrected as shown below:

In the Claims

In Claim 3, at Column 6, Line 3, delete "first".

In Claim 5, at Column 6, Line 12, delete "first".

In Claim 8, at Column 6, Lines 29 and 30, change "first heat exchanger" to --heat exchanger--.

In Claim 9, at Column 6, Line 37, delete "first".

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*